United States Statutory Invention Registration [19]

[11] Reg. Number: H990

Kayser

[43] Published: Nov. 5, 1991

[54] RECRYSTALLIZATION OF 3-NITRO-1,2,4-TRIAZOL-5-ONE FROM DIMETHYLSULFOXIDE AND METHYLENE CHLORIDE

[75] Inventor: Eleonore G. Kayser, Baltimore, Md.

[73] Assignee: The United States of America as represented by the Secretary of the Navy, Washington, D.C.

[21] Appl. No.: 386,378

[22] Filed: Jul. 26, 1989

[51] Int. Cl.[5] ..... C07D 249/12; C07D 249/14

[52] U.S. Cl. ..... 548/263.8

*Primary Examiner*—Robert L. Stoll
*Assistant Examiner*—Joseph D. Anthony
*Attorney, Agent, or Firm*—Kenneth E. Walden; Roger D. Johnson

[57] ABSTRACT

The production of 3-nitro-1,2,4-triazol-5-one (NTO) having finely divided particles of uniform size by dissolving conventionally produced large, jagged, rods of NTO in hot dimethylsulfoxide and then injecting the hot solution through a small orifice into methylene chloride at a temperature of from about −10° C. to about 30° C.

5 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

RECRYSTALLIZATION OF 3-NITRO-1,2,4-TRIAZOL-5-ONE FROM DIMETHYLSULFOXIDE AND METHYLENE CHLORIDE

BACKGROUND OF THE INVENTION

This invention relates to hetrocylic organic explosives and more particularly to nitrated tetrazoles.

3-nitro-1,2,4-triazol-5-one (NTO) is typically recrystallized in water. Unfortunately, NTO recrystallizes from water in relatively large, jagged rod-like particles that have a tendency to agglomerate. The irregular and jagged crystal shapes cause the mixing of the explosive formulations with NTO to be highly viscous and difficult to process and to pour. As a result, the amount of NTO which can be used in a processable explosive composition is limited and the performance of the explosive is therefore reduced.

SUMMARY OF THE INVENTION

Accordingly, an object of this invention is to provide a method of obtaining small particle size 3-nitro-1,2,4-triazol-5-one (NTO).

Another object of this invention is to provide NTO having a uniform particle size.

A further object of this invention is to provide NTO in a form suitable for use as a booster explosive material.

These and the other objects of this invention are accomplished by providing a process for producing finely divided 3-nitro-1,2,4-triazol-5-one (NTO) comprising:

(1) dissolving 3-nitro-1,2,4-triazol-5-one (NTO) in hot dimethylsulfoxide (DMSO);

(2) injecting the hot NTO/DMSO solution through an opening of 0.70 mm or less into methylene chlorine at room temperature; and (3) isolating the finely divided particles of 3-nitro-1,2,4-triazol-5-one (NTO) which are produced in step (2).

DETAILED DESCRIPTION OF THE PREFERRED EMBODIMENT

In the present process the large, jagged, needlelike 3-nitro-1,2,4-triazol-5-one (NTO) crystals are first dissolved in hot dimethylsulfoxide (DMSO). The hot DMSO is preferably at a temperature of from about 60° C. to about 90° C., and more preferable from 70° C. to 80° C. The DMSO is preferably saturated with the NTO. At this time insoluble impurities may be removed by filtration.

Next a fine stream of the hot NTO/DMSO solution is injected into methylene chloride which is kept at a temperature of from about -10° C. to about 30° C. and more preferably from 0° C. to 25° C., and still more preferably at from 5° C. to 15° C. The fine stream of NTO/DMSO is created by injecting the solution through an opening (e.g., jet or tube) having an internal diameter of 0.70 mm or less and preferably of 0.40 mm or less. The lower limit on the diameter of the tube is determined by practical considerations such as what size tubing is available and at what rate the crystals are to be produced.

Another variation of this invention is to blow a stream of atomized NTO/DMSO solution in an inert gas (argon, helium nitrogen, etc.) into the methylene chloride. In this manner much smaller purer crystals of NTO will be produced.

The product crystals of NTO are then collected and washed with methylene chloride (or a similar solvent). Finally, the NTO is dried at from about 45° C. to about 55° C. under vacuum.

The general nature of the invention having been set forth, the following example is presented as specific example thereof. It will be understood that this invention is not limited to this specific example but is susceptible to various modifications that will be recognized by one of ordinary skill in the art.

EXAMPLE

Approximately 3.0 to 3.5 grams of large particle size (2,702 $cm^2/cm^3$) 3-nitro-1,2,4-triazol-5-one (NTO) was dissolved in 4 to 5 ml of hot dimethylsulfoxide (DMSO) at a temperature of 70° C. This NTO/DMSO solution was then injected through a No. 27 needle into 150 ml of methylene chloride at room temperature. The NTO/DMSO/methylene chloride mixture was filtered and the collected solid was washed 3 times with approximately 100 ml of methylene chloride and filtered. The solid was dried under vacuum at approximately 50° C. to a constant weight. This process increased the surface area of the NTO from 2,702 $cm^2/cm^3$ to 56,742 $cm^2/cm^3$. Blowing a stream of the atomized NTO/DMSO solution in an inert gas (nitrogen) into the methylene chloride increased the surface area of the NTO to 68,515 $cm^2/cm^3$.

Obviously, numerous modifications and variations of the present invention are possible in light of the above teachings. It is therefore to be understood that within the scope of the appended claims the invention may be practiced otherwise than as specifically described.

What is claimed is:

1. A process for producing finely divided 3-nitro-1,2,4-triazol-5-one of uniform particle size comprising:

(1) dissolving conventional large, jagged, rodlike 3-nitro-1,2,4-triazol-5-one crystals having a particle size of (2,702 $cm^2/cm^3$ in hot dimenthylsulfoxide at a temperature of from about 60° C. to about 90° C.;

(2) injecting the hot dimethylsulfoxide solution through an opening of 0.70 mm or less in diameter in methylene chloride which is kept at a temperature of from about −10° C. to about 30° C.; and (3) isolating the finely divided particles of 3-nitro-1,2,4-triazol-5-one which are produced in step (2).

2. The process of claim 1 wherein the hot dimethylsulfoxide in step (1) is at a temperature of from 70° C. to 80° C.

3. The process of claim 1 wherein the methylene chloride in step (2) is maintained at a temperature of from 0° C. to 25° C.

4. The process of claim 3 wherein the methylene chloride in step (2) is maintained at a temperature of from 5° C. to 15° C.

5. The process of claim 1 wherein the opening in step (1) is 0.40 mm or less in diameter.

* * * * *